United States Patent [19]

Wight

[11] 4,169,111

[45] Sep. 25, 1979

[54] MANUFACTURE OF ETHYLBENZENE

[75] Inventor: Carlyle G. Wight, Fullerton, Calif.

[73] Assignee: Union Oil Company of California, Brea, Calif.

[21] Appl. No.: 874,375

[22] Filed: Feb. 2, 1978

[51] Int. Cl.² .......................... C07C 3/52; C07C 3/62
[52] U.S. Cl. ..................... 585/323; 585/467; 585/474; 585/906; 585/314
[58] Field of Search .................... 260/671 R, 672 T

[56] References Cited

U.S. PATENT DOCUMENTS

| 3,255,269 | 6/1966 | Gilman et al. | 260/671 R |
| 3,691,245 | 9/1972 | Helzner | 260/671 R |
| 3,751,504 | 8/1973 | Keown et al. | 260/671 R |
| 3,769,360 | 10/1973 | Harper et al. | 260/671 R |
| 3,772,398 | 11/1973 | Carr et al. | 260/671 R |
| 3,776,971 | 12/1973 | Carr et al. | 260/671 R |
| 3,843,739 | 10/1974 | Harper et al. | 260/672 T |
| 3,929,672 | 12/1975 | Ward | 252/455 Z |
| 4,009,217 | 2/1977 | Uitti | 260/671 R |
| 4,016,218 | 4/1977 | Haag et al. | 260/671 R |
| 4,028,227 | 6/1977 | Gustafson | 252/216 |
| 4,079,093 | 3/1978 | Winter | 260/671 R |

Primary Examiner—C. Davis
Attorney, Agent, or Firm—Richard C. Hartman; Dean Sandford; Cleveland R. Williams

[57] ABSTRACT

Benzene is alkylated with ethylene in the presence of a crystalline zeolite catalyst to produce ethylbenzene and polyethylbenzenes. At least a portion of the diethylbenzene fraction is recycled to the alkylation zone while the remainder thereof plus the higher polyethylbenzenes are subjected to transalkylation with benzene in a separate transalkylation zone to produce additional ethylbenzene.

12 Claims, 1 Drawing Figure

DEB = DIETHYLBENZENE
TEB = TRIETHYLBENZENE

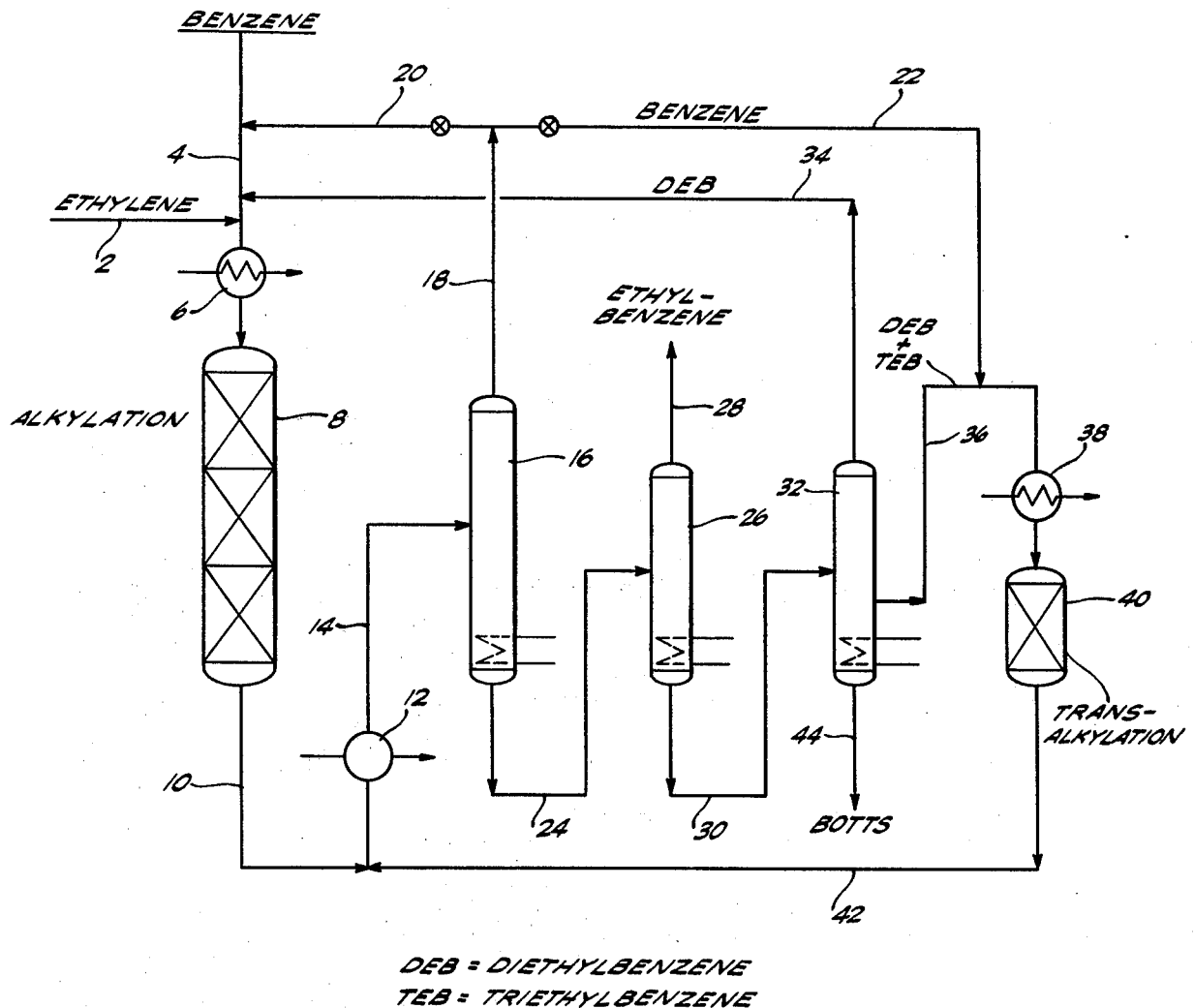

MANUFACTURE OF ETHYLBENZENE

BACKGROUND AND SUMMARY OF INVENTION

The use of crystalline aluminosilicate zeolites for catalyzing the alkylation of benzene with olefins is now well known in the art. It is customary in such processes to utilize a fairly large mole-excess of benzene in order to minimize polymerization of the olefin, as well as to promote the formation of monoalkyl benzene and suppress the formation of polyalkyl benzenes. The polyalkyl benzenes are in many cases subjected to transalkylation with benzene to produce additional monoalkylbenzene. Such transalkylation can be effected either in a separate transalkylation zone, or by recycling the polyalkylbenzenes to the alkylation zone.

A major problem associated with such zeolite-catalyzed alkylations has been that of catalyst deactivation rates, which usually limit run lengths to no more than a few weeks before the catalyst must be regenerated. It has been fairly well established that the mechanism of deactivation involves polymerization of the olefin, followed by hydrogen-transfer and cyclization reactions to form large aromatic molecules which cannot diffuse out of the crystal micropores of the zeolite in which the active sites are located. (Venuto et al, *J. Catalysis* 5, 484–493, 1966; *I and EC Product Research and Development*, 6, 190–192, Sept. 1967).

In alkylating benzene with ethylene using a catalyst of this invention (in the form of 1/16" cylindrical extrudates) and with no recycle of polyalkylbenzenes to the alkylation zone, the catalyst deactivation rate was such as to indicate a maximum run length of about 93 days under a specific set of operating conditions. Under the same conditions, but with recycle of the diethyl- and triethylbenzene product fraction to the alkylation zone, the deactivation rate was such as to indicate a maximum run length of only about 55 days. However, most unexpectedly, in two separate run periods in which only the diethylbenzene product fraction was recycled, there was essentially no detectable catalyst deactivation, indicating a run length of at least one year or more. Apparently, the presence of diethylbenzenes at the inception of alkylation, i.e., at the inlet end of the reactor where the concentration of ethylene is still high, in some manner stabilizes the system, an effect which is destroyed by the presence of triethylbenzenes, or possibly some polymer which cannot be readily separated from triethylbenzenes by distillation.

According to the present invention therefore, diethylbenzenes, but essentially no triethylbenzenes, are recycled to the alkylation zone to achieve a stable long-lived alkylation cycle. However, to achieve this objective it is not necessary, nor is it desirable, to recycle all of the diethylbenzene fraction. Maximum transalkylation efficiency generally requires higher temperatures than are optimum for alkylation, and hence a separate transalkylation zone is provided to which benzene, a large proportion of the diethylbenzenes, and all of the triethylbenzenes and higher alkylated products are fed for conversion to ethylbenzene. Another advantage is not recycling all of the diethylbenzene fraction is that the distillation load is reduced since it is not necessary to make a sharp separation between diethylbenzenes and triethylbenzenes.

PRIOR ART

U.S. Pats. Nos. 3,772,398 and 3,776,971 disclose the alkylation of benzene with olefins using zeolite catalysts, while recycling more than the equilibrium proportion of dialkylbenzenes. Separate transalkylation is not disclosed, nor is there any disclosure of the disposition of trialkylbenzenes. All the data relates to the alkylation of benzene with propylene to produce cumene, and there is no suggestion of any improvement in catalyst cycle life as a result of recycling di-isopropylbenzenes.

BRIEF DESCRIPTION OF DRAWING

The drawing is a simplified flow diagram illustrating the invention in its preferred form.

DETAILED DESCRIPTION

Referring now to the drawing, ethylene is brought in via line 2 and mixed in line 4 with the predetermined proportions of makeup benzene, recycle benzene and diethylbenzenes. The mixture is then passed through preheater 6 and thence into adiabatic reactor 8 filled with a bed or beds of alkylation catalyst to be described hereinafter. In reactor 8, the ethylene is rapidly consumed in the upper portion of the catalyst bed, generating therein an ascending temperature profile which levels out to a maximum value in the lower part of the reactor in which relatively non-exothermic transalkylation reactions take place. It will be understood that the pre-heating in preheater 6 should be controlled, depending on feed composition, to yield the desired maximum temperature in reactor 8. Suitable conditions for the alkylation are as follows:

| | Alkylation Conditions | |
|---|---|---|
| | Broad Range | Preferred Range |
| Max. Temp., °F. | 300–900 | 350–600 |
| Pressure, psig | 150–2000 | 400–1500 |
| Total WHSV | 2–2000 | 4–100 |
| Benzene/Ethylene Mole-Ratio | 2–20 | 4–15 |
| Diethylbenzene/Benzene Mole-Ratio in Feed | .0001–0.02 | .0005–.008 |

The conditions of temperature and pressure should preferably be correlated so that a liquid phase is present. A somewhat more rapid catalyst deactivation occurs under most alkylating conditions when no liquid phase is present, presumably due to the deposition of polymer precursors which are not washed away.

The effluent from reactor 8 will normally contain, per 100 moles of total alkylbenzenes, about 80–95 moles of ethylbenzene, 5–15 moles of diethylbenzenes and 1–4 moles of higher alkylated benzenes, plus excess unreacted benzene. This mixture is withdrawn via line 10, depressured and cooled to distillation temperature in condenser 12 and passed via line 14 to distillation column 16. Unreacted benzene is taken overhead via line 18 and recycled in part via line 20 to alkylation reactor 8, and in part via line 22 to the transalkylation zone described hereinafter.

Bottoms product from column 16 is transferred via line 24 to distillation column 26, from which product ethylbenzene is taken overhead via line 28. Bottoms product from column 26 is transferred via line 30 to distillation column 32, which is operated to provide a substantially pure diethylbenzene overhead in line 34, amounting to between about 10% and 90%, preferably about 20-60%, of the total diethylbenzenes fed to the column. This overhead fraction is recycled to alkylation reactor 8, while a side-cut containing the remaining diethylbenzenes plus the triethylbenzenes and higher alkylated benzenes is withdrawn via line 26, blended with recycle benzene from line 22, and passed via preheater 38 into transalkylation reactor 40 containing a zeolite catalyst which may be the same as, or different than, the catalyst employed in reactor 8. Suitable transalkylation conditions may be summarized as follows:

| Transalkylation Conditions | | |
|---|---|---|
| | Broad Range | Preferred Range |
| Temp., °F. | 350-900 | 450-650 |
| Pressure, psig | 150-2000 | 400-1000 |
| Total WHSV | 1-20 | 2-10 |
| Mole-Ratio, | | |
| Benzene/Ethyl Side Chains | 2-20 | 4-10 |

In the transalkylation zone, ethyl groups are equilibrated from polyalkylbenzenes to benzene to form additional ethylbenzene, as e.g.:

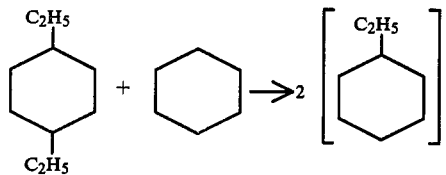

The resulting effluent from reactor 40 is transferred via line 42 to fractionating columns 16, 26 and 32 to recover benzene, ethylbenzene and polyalkylbenzenes, along with the effluent from reactor 8.

In order to prevent the buildup of heavy polymers in the system, it is preferred that a small bottoms stream, boiling above about 550° F., be withdrawn from column 32 via line 44.

The catalyst(s) employed in reactors 8 and 40 are now well known in the art, consisting of crystalline aluminosilicates having $SiO_2/Al_2O_3$ mole ratios between about 2 and 80, preferably about 4-12, and a predominance of crystal pore volume in pores having diameters between about 5 and 15 Å. A critical aspect of the invention resides in substantially completely removing zeolitic alkali metal and alkaline earth metals from the zeolite, and replacing such metals with hydrogen ions and/or rare earth metals. The $Na_2O$ content of the zeolite should be less than about 0.7%, preferably less than about 0.5% by weight. Only highly acidic zeolites of this nature possess the desired activity—and the concomitant high deactivation rates which the present invention is designed to control.

Examples of suitable zeolites include molecular sieves of the X, Y, L, B, ZSM-5 and Omega crystal types, as well as mordenite, chabazite and the like. A much preferred zeolite is steam stabilized hydrogen Y zeolite having a unit cell size between about 24.40 and 24.64 Å, and having been prepared by the method described in U.S. Pat. No. 3,929,672, the disclosure of which is incorporated herein by reference.

In order to prepare mechanically stable extrudates of the crystalline zeolites, a porous mineral oxide binder is utilized, such as alumina gel, silica-gel, silica-alumina cogel, plastic acid-washed clays, titania, zirconia and the like, with alumina being preferred. Ordinarily the finished catalyst comprises about 3-50%, preferably about 5-30% by weight of the binder, which serves not only to strengthen the extrudates, but to provide a porous matrix comprising macropores in the 300-1000 Å diameter range. These macropores can be regarded as "freeways", giving improved diffusional access to the interior of the extrudates.

The catalysts are preferably utilized in the form of extrudates having a diameter between about 1/32" and 1/8". The extrudates may have a circular cross section, or preferably they may be shaped into various non-circular configurations embracing a plurality of arcuate lobes extending outwardly from the central portion thereof, as illustrated for example in FIGS. 6, 7, 8, and 10 of U.S. Pat. No. 4,028,227. These configurations lend strength to the extrudates and also provide more interstitial void space in the catalyst bed, thereby reducing pressure drop. It is further preferred that the ratio of exterior surface area to volume of the extrudates should be within the range of 85-160 in $^{-1}$, preferably 90-150 in $^{-1}$. It has been found that maintaining a high ratio of exterior surface area to volume improves diffusional transfer of reactants into, and products out of, the catalyst particles with resultant improvements in selectivity, efficiency and catalyst life.

The following examples are illustrative of the invention:

EXAMPLE 1

The catalyst utilized in the following examples was prepared by comulling about 10 weight-percent (dry basis) of an alumina hydrogel with 90 weight-percent of a steam stabilized ammonium Y zeolite containing about 0.2% $Na_2O$ and having been prepared by the method described in U.S. Pat. No. 3,929,672. The comulled mixture was then formed into extrudates in conventional manner by extrusion through a circular 1/16" diameter die, followed by drying and calcining at 860° F.

EXAMPLE 2

About 158 ml of the catalyst of Example 1 (mixed with 317 ml of quartz chips) was loaded into a 2.17 in. I.D. reactor. A bed of quartz chips was provided above the catalyst bed for preheating the feed. The entire reactor was enclosed within a molten salt bath to provide quasi-isothermal conditions. Temperature profile in the catalyst bed was monitored by a vertically moveable thermocouple. A 7-day alkylation run was carried out in which benzene was continuously ethylated with ethylene under the following conditions (with recycle of benzene, but no polyalkyl benzenes to the reactor):

| | |
|---|---|
| Reactor Bath Temp. | 440° F. |
| Pressure | 500 psig |
| Total WHSV | 10.7 |
| Benzene/Ethylene Mole-Ratio | 8.5/1.0 |

Under these conditions the ethylene was substantially completely consumed in the upper portion of the catalyst bed, as evidenced by a peak in the temperature profile. This peak exceeds the liquid bath temperature by about 45°-55° F., and results from the exothermic alkylation of benzene with ethylene. After substantial depletion of ethylene, the peak temperature drops off essentially to the bath temperature. During the next 7 days of operation the peak moved downwardly at an essentially linear average rate to a level 25% down the catalyst bed from a beginning-of-run position 18.8% down in the catalyst bed. This downward shift in the position of the peak temperature provides a measure of the catalyst deactivation rate. In the present example the 7 day shift shows that an average of about 0.86% per day of the catalyst bed was being deactivated. This indicates a maximum cycle life of about 93 days before breakthrough of ethylene in the reactor effluent.

EXAMPLE 3

Diethylbenzene Recycle

Operation as described in Example 2 was continued for an additional 10 days, during which period the diethylbenzene product fraction was continuously recycled to the reactor at the rate of about 16 g/hr, providing an average mole-ratio of diethylbenzene/benzene of about 0.0107/1.0. Periodic monitoring of the peak temperature position gave the following results:

TABLE 1

| Run Interval, Hours | Position of Peak Temp., Percent of Catalyst Bed from Top |
|---|---|
| 20 | 25.0 |
| 43 | 26.6 |
| 69 | 23.4 |
| 140 | 25.8 |
| 164 | 25.0 |
| 187 | 25.0 |
| 235 | 25.0 |

These figures indicate a substantially nil deactivation rate, with a run length of at least one year clearly to be expected, barring any process upsets.

EXAMPLE 4

Diethylbenzenes Triethylbenzenes Recycle

Operation as described in Example 3 was continued an additional 10.5 days, with the exception that instead of recycling diethylbenzenes only, the diethylbenzene plus triethylbenzene fraction was recycled at the rate of about 20.6 g/Hr. Periodic monitoring of the peak temperature position gave the following results:

TABLE 2

| Run Interval, Hours | Position of Peak Temp., Percent of Catalyst Bed from Top |
|---|---|
| 72 | 26.6 |
| 78 | 28.1 |
| 96 | 29.7 |
| 144 | 31.3 |
| 168 | 32.0 |
| 198 | 35.9 |
| 222 | 35.9 |
| 256 | 40.2 |

The figures show that an average of approximately 1.45% per day of the catalyst bed was being deactivated, which would give a maximum run length of about 55 days before the peak temperature reaches the bottom of the catalyst bed.

EXAMPLE 5

Recycle of Diethylbenzenes

Operation as described in Example 3 was resumed for an additional 8 days, with recycle of diethylbenzenes only. Periodic monitoring of the peak temperature position gave the following results:

| Run Interval, Hours | Position of Peak Temp., Percent of Catalyst Bed from Top |
|---|---|
| 24 | 40.2 |
| 50 | 42.2 |
| 72 | 40.6 |
| 102 | 40.6 |
| 147 | 40.6 |
| 169 | 40.6 |
| 191 | 40.6 |

It is evident that recycle of diethylbenzenes again stabilized the system, giving a nil deactivation rate. It is also apparent however that resuming the recycle of diethylbenzenes did not reverse the deactivation which occured in Example 4 due to the presence of the triethylbenzene fraction.

The following claims and their obvious equivalents are believed to define the true scope of the invention:

I claim:

1. A process for the manufacture of ethylbenzene which comprises:
   (1) passing a feed mixture of ethylene and a mole-excess of benzene through a fixed bed of an alkylation catalyst under alkylation conditions controlled to consume essentially all of said ethylene with resultant production of ethylbenzene, diethylbenzenes and triethylbenzenes, said catalyst comprising an acidic crystalline aluminosilicate zeolite containing less than about 0.7 wt. % of $Na_2O$;
   (2) separating the product from step (1) into fractions comprising (a) a benzene fraction, (b) a substantially pure ethylbenzene fraction, (c) a substantially pure diethylbenzene fraction, and (d) a fraction comprising substantially all of said triethylbenzenes; and
   (3) recycling at least a portion of fraction (c), but essentially none of fraction (d), to mingle with said feed mixture of step (1).

2. A process as defined in claim 1 wherein said aluminosilicate zeolite is a steam stabilized hydrogen Y zeolite having a unit cell size between about 24.40 and 24.64 Å.

3. A process as defined in claim 1 wherein the mole-ratio of benzene/ethylbenzene in said feed mixture is between about 2 and 20.

4. A process as defined in claim 3 wherein sufficient of said fraction (c) is recycled to step (1) to provide a moleratio of diethylbenzenes/benzene in said feed mixture of between about 0.0001 and 0.02.

5. A process as defined in claim 4 wherein said alkylation is carried out at a maximum temperature of about 350°–600° F.

6. A process for the manufacture of ethylbenzene which comprises:
   (1) passing a feed mixture of ethylene and a mole-excess of benzene through a fixed bed of an alkylation catalyst under alkylation conditions controlled to consume essentially all of said ethylene with resultant production of ethylbenzene, diethylbenzenes and triethylbenzenes, said catalyst comprising an acidic crystalline aluminosilicate zeolite containing less than about 0.7 wt.% of $Na_2O$;
   (2) separating the product from step (1) into fractions comprising (a) a benzene fraction, (b) a substantially pure ethylbenzene fraction, (c) a substantially pure diethylbenzene fraction, and (d) a fraction comprising substantially all of said triethylbenzenes;

(3) recycling fraction (c) to mingle with said feed mixture in step (1); and (4) subjecting fraction (d) to transalkylation in admixture with benzene in the absence of ethylene, and in contact with a zeolite catalyst as defined in step (1) to produce additional ethylbenzene.

7. A process as defined in claim 6 wherein said fraction (c) comprises from about 10–90% of the diethylbenzenes from step (1), and fraction (d) comprises the remainder of said diethylbenzenes from step (1).

8. A process as defined in claim 6 wherein said fraction (c) comprises from about 20–60% of the diethylbenzenes from step (1), and fraction (d) comprises the remainder of said diethylbenzenes from step (1).

9. A process as defined in claim 6 wherein said aluminosilicate zeolite is a steam stabilized hydrogen Y zeolite having a unit cell size between about 24.40 and 24.64 Å.

10. A process as defined in claim 6 wherein the mole-ratio of benzene/ethylene in said feed mixture is between about 2 and 20.

11. A process as defined in claim 10 wherein said fraction (c) contains sufficient diethylbenzenes to provide a mole-ratio of diethylbenzenes/benzene in said feed mixture of between about 0.0001 and 0.02.

12. A process as defined in claim 11 wherein said alkylation is carried out at a maximum temperature of about 350°–600° F.

* * * * *